United States Patent
Feiweier

(10) Patent No.: US 12,399,246 B2
(45) Date of Patent: Aug. 26, 2025

(54) TECHNIQUES FOR DIFFUSION IMAGING

(71) Applicant: Siemens Healthcare GmbH, Erlangen (DE)

(72) Inventor: Thorsten Feiweier, Poxdorf (DE)

(73) Assignee: Siemens Healthineers AG, Erlangen (DE)

( * ) Notice: Subject to any disclaimer, the term of this patent is extended or adjusted under 35 U.S.C. 154(b) by 431 days.

(21) Appl. No.: 17/308,386

(22) Filed: May 5, 2021

(65) Prior Publication Data
US 2021/0349168 A1 Nov. 11, 2021

(30) Foreign Application Priority Data

May 6, 2020 (DE) .......................... 102020205692.7

(51) Int. Cl.
*A61B 5/00* (2006.01)
*A61B 5/055* (2006.01)
(Continued)

(52) U.S. Cl.
CPC ........ *G01R 33/56341* (2013.01); *A61B 5/055* (2013.01); *A61B 5/70* (2013.01); *G01R 33/5616* (2013.01)

(58) Field of Classification Search
CPC .......... G01R 33/56341; G01R 33/5616; G01R 33/5602; A61B 5/055; A61B 5/70
See application file for complete search history.

(56) References Cited

U.S. PATENT DOCUMENTS

| | | |
|---|---|---|
| 2004/0140803 A1 | 7/2004 | Deimling |
| 2013/0187649 A1 | 7/2013 | Bhat et al. |

(Continued)

FOREIGN PATENT DOCUMENTS

| | | |
|---|---|---|
| CA | 2936624 A1 | 8/2015 |
| CN | 1499218 A | 5/2004 |

(Continued)

OTHER PUBLICATIONS

Szczepankiewicz, Linear, planar and spherical tensor-valued diffusion MRI data by free waveform encoding in healthy brain, water, oil and liquid crystals, 2019 (Year: 2019).*
Westin et al., "Q-space trajectory imaging for multidimensional diffusion MRI of the human brain," HHS Public Access, Neuroimage, vol. 135, pp. 345-362 (2016).

(Continued)

*Primary Examiner* — Jeffrey G Hoekstra
*Assistant Examiner* — Gabriel Victor Popescu
(74) *Attorney, Agent, or Firm* — Banner & Witcoff Ltd.

(57) ABSTRACT

The disclosure relates to techniques for diffusion imaging of an examination region of a patient using a magnetic resonance facility. The technique may include specifying a number, which is at least two, of diffusion gradient pulse sequences for recording diffusion data sets using the magnetic resonance facility such that the diffusion gradient pulse sequences have a b-matrix that describes a planar diffusion encoding. The matrix may have precisely two intrinsic values that differ from zero. The technique may further include recording the diffusion data sets with the specified diffusion gradient sequences, and acquiring a trace-weighted image data set by geometric averaging of the at least two diffusion data sets. The diffusion gradient pulse sequences are determined such that the sum of all the b-matrices results in the unit matrix multiplied by a factor that characterizes the diffusion weighting (e.g. a predetermined b-value) and the number divided by three.

15 Claims, 2 Drawing Sheets

Figure 1:
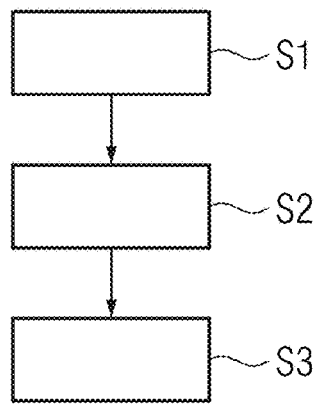

(51) Int. Cl.
  *G01R 33/561*  (2006.01)
  *G01R 33/563*  (2006.01)

(56) References Cited

U.S. PATENT DOCUMENTS

| | | | |
|---|---|---|---|
| 2016/0291113 A1 | 10/2016 | Stemmer | |
| 2016/0356873 A1* | 12/2016 | Topgaard | G01R 33/5608 |
| 2019/0072630 A1* | 3/2019 | Feiweier | G01R 33/56341 |
| 2019/0377050 A1* | 12/2019 | Ennis | G01R 33/56341 |
| 2021/0208229 A1* | 7/2021 | Seethamraju | G01R 33/56341 |
| 2022/0221542 A1* | 7/2022 | Teh | G01R 33/56341 |

FOREIGN PATENT DOCUMENTS

| | | |
|---|---|---|
| CN | 103211596 A | 7/2013 |
| CN | 106019190 A | 10/2016 |
| DE | 102015205693 A1 | 10/2016 |
| DE | 102017215444 A1 | 3/2019 |
| IN | 201617026545 A | 8/2016 |
| WO | 02068978 A2 | 9/2002 |

OTHER PUBLICATIONS

Wong et al., "Optimized Isotropic Diffusion Weighting," MRM, vol. 34, pp. 139-143 (1995).
Sczepankiewicz et al., "Linear, planar and spherical tensor-valued diffusion MRI data by free waveform encoding in healthy brain, water, oil and liquid crystals," Elsevier Inc., Data in Brief, vol. 25 (2019).
Basser et al., "Estimation of the Effective Self-Diffusion Tensor from the NMR Spin Echo," Journal of Magnetic Resonance, Series B 103, pp. 247-254 (1994).
Shemesh et al., "Conventions and Nomenclature for Double Diffusion Encoding NMR and MRI," Magnetic Resonance in Medicine, vol. 75, pp. 82-87 (2016).
Bernstein, M., et al., "Handbook of MRI Pulse Sequences", Elsevier Academic Press, 39 pgs., 2004.
Li Cuining, "Study on Diffusion Tensor Imaging in Healthy Human Brain and Cerebral Ischemia Disease"; 15. Jan. 2011; Doctoral Electronic Journal (See English Abstract at p. 4 et seq.).
Bates Alice et al.; "A 4D Basis and Sampling Scheme for the Tensor Encoded Multi-Dimensional Diffusion MRI Signal"; 15. Aug. 2019; IEEE Signal Processing Letters.

* cited by examiner

TECHNIQUES FOR DIFFUSION IMAGING

CROSS-REFERENCE TO RELATED APPLICATIONS

The present application claims the benefit of the filing date of German patent application no. DE 10 2020 205 692.7, filed on May 6, 2020, the contents of which are incorporated herein by reference in their entirety.

TECHNICAL FIELD

The disclosure relates to diffusion imaging of an examination region of a patient with a magnetic resonance imaging apparatus, in which a trace-weighted image data set is acquired. The disclosure additionally relates to a magnetic resonance imaging apparatus, a computer program, and an electronically readable data carrier.

BACKGROUND

Alongside other imaging techniques in magnetic resonance imaging, diffusion imaging has gained considerably in importance in the past few years. The development of diffusion imaging (diffusion-weighted magnetic resonance imaging, "Diffusion-Weighted Imaging"—DWI) is based on the pulsed gradient spin echo technique (PGSE) first proposed in the mid-1960s by Edward Stejskal and John Tanner for measuring diffusion-weighted echo signals. It has now been further developed in a variety of ways.

Diffusion imaging is characterized in that the diffusion of water molecules is exploited to generate a contrast in magnetic resonance image data sets. In this way, the process of the diffusion of molecules can be imaged in biological tissues. To be able to survey the diffusion processes, additional diffusion gradient pulses that sensitively shape the magnetic resonance sequence to the motion are used in a magnetic resonance sequence alongside the imaging gradient pulses. The diffusion in biological tissues can frequently be described as anisotropic. Although applications are known in which this anisotropy is the aim of the examination and the individual components of the diffusion tensor are measured, in other applications it may happen that the anisotropy is considerable and conceals underlying changes in the local apparent diffusion coefficient (ADC). In these and other circumstances, it is preferable to determine the trace of the diffusion tensor once the latter is independent of the orientation. Corresponding imaging approaches are also referred to as diffusion imaging or as trace-weighted diffusion imaging.

SUMMARY

In clinical magnetic resonance-diffusion imaging, trace-weighted image data sets and parameter maps derived therefrom, for example of the apparent diffusion coefficient or ADC, form the basis for the detection of microstructural changes in the tissue such that they are useful, for example, in the diagnosis of strokes or dynamic tumor processes in the human body.

In conventional diffusion encoding via corresponding diffusion gradient pulse sequences, with each recording of a diffusion data set, the microscopic motion of the signal-generating nuclear spins is examined along a specific spatial direction, which is why this type of diffusion encoding is also referred to as linear coding. From at least three images, that is from three diffusion data sets with different coding directions, a trace-weighted image data set can then be calculated.

As a measure of how sensitive a measurement is to diffusion motion, what is known as the b-value is usually used in literature. In the spatial description, the b-matrix indicates how this sensitivity is distributed in space. Yet in clinical applications, for example, b-values in the range from 500 to 2000 s/mm$^2$ are sought after, yet procedures are also known in which a trace-weighted image data set is to be determined for a plurality of b-values.

For the linear diffusion encoding that has already been mentioned, diffusion gradient pulse sequences are used for which the b-matrix has precisely one intrinsic value that differs from zero for each individual measurement, which is for each recording of a diffusion data set. In order to be able to determine a trace-weighted image data set therefrom, the b-matrices $b_n$ of the at least N=3 encoding directions must fulfill the following condition:

$$N/3 b1 = \Sum_{n=1 \ldots N} b_n, \quad (1)$$

where 1 is the unit matrix and b is the b-value. Then, a trace-weighted image data set can be calculated from the individual diffusion-weighted diffusion data sets:

$$S_n(r) = S_0(r)\exp(-\mathrm{Tr}(D(r)b_n)) \quad (2)$$

according to $$S_{Trace}(r) = \prod_{n=1 \ldots N} S_n(r)^{1/N} \quad (3)$$
$$= S_0(r)\exp\left(-1/N \mathrm{Tr}\left(D(r) \sum_{n=1 \ldots N} b_n\right)\right)$$
$$= S_0(r)\exp(-b/3 \mathrm{Tr}(D(r)))$$

Here, D(r) stands for the symmetrical 3×3 diffusion tensor at location r, Tr for the trace formation operation (sum of the diagonal elements), and $S_0(r)$ for the magnetic resonance signal that would be received without diffusion-weighting. The so-called apparent diffusion coefficient (ADC) is defined in this context as:

$$\mathrm{ADC} = \tfrac{1}{3}\mathrm{Tr}(D(r)). \quad (4)$$

The advantage of linear diffusion encoding is that it is extremely efficient, and therefore a high b-value of the corresponding diffusion gradient pulse sequence can be achieved within a short period of time. Moreover, an independent calculation of trace-weighted image data sets is facilitated for each individual b-value. Nevertheless, three measurements are disadvantageously required to be able to determine the trace-weighted image data set. Furthermore, the trace-weighting is influenced by microscopic anisotropy and mesoscopic orientation dispersion, as is demonstrated for example in an article by Filip Szczepankiewicz et al., "Linear, planar and spherical tensor-valued diffusion MRI data by free waveform encoding in healthy brain, water, oil and liquid crystals", *Data in Brief* 25 (2019) 104028.

As a further approach to the determination of trace-weighted image data sets in diffusion imaging, so-called spherical diffusion encoding was proposed, see for example the article by Eric C. Wong et al., "Optimized isotropic diffusion weighting", *Magnetic Resonance in Medicine* 34 (1995), pp. 139-143. Here, only one single diffusion data set has to be recorded, which directly corresponds to the trace-weighted image data set. A diffusion gradient pulse sequence is used having a b-matrix that comprises three virtually identical intrinsic values that differ from zero, $b_1 = b_2 = b_3 = b/$ 3. It can therefore be represented as b=b/3 1. Thus, just one individual spherically diffusion encoded diffusion data set can reproduce a trace-weighting, $$S(r)=S_0(r)\exp(-\text{Tr}(D(r)b))=S_0(r)\exp(-b/3\text{Tr}(D(r))) \quad (5)$$

Spherical diffusion encoding advantageously requires only one measurement, allows the recording of trace-weighted image data sets for each individual b-value, and its trace-weighting is influenced only by the microscopic anisotropy. However, spherical diffusion encoding is disadvantageously very inefficient, which means that longer periods of time are required to achieve the desired b-values.

As a further alternative procedure, it has been proposed that a trace-weighting, or specifically the trace-weighted image data set, be calculated from a tensor estimate, see the article by Peter J. Basser et al., "Estimation of the effective self-diffusion tensor from the NMR spin echo", *Journal of Magnetic Resonance*, Series B 103 (1994), pp. 247-254. Here, the complete diffusion tensor D(r) from all the recorded diffusion data sets and the magnetic resonance signal is estimated using known methods without diffusion weighting $S_0(r)$. From this, trace-weighted image data sets can be acquired mathematically for a given b-value, as:

$$S_0(r)\exp(-b/3\text{Tr}(D(r))). \quad (6)$$

This approach has the advantage that the complete diffusion tensor is acquired, from which further parameter maps can be determined, and that an extremely efficient encoding is provided; to be specific, linear diffusion encoding can be used. Disadvantageously, however, this approach requires at least seven measurements with at least six different encoding directions and at least two different diffusion weightings, and therefore b-values. An independent determination of trace-weighted image data sets for an individual b-value is not possible, since at least two diffusion weightings are input. Finally, the tensor estimation, and thus the trace-weighting too, are influenced by microscopic anisotropy and mesoscopic orientation-dispersion.

The disclosure therefore addresses the problem of providing an efficient procedure for acquiring a trace-weighted image data set, requiring fewer measurements, and is less influenced by microscopic anisotropy or mesoscopic orientation-dispersion.

To solve this problem, a method for diffusion imaging of an examination region of a patient using a magnetic resonance imaging apparatus comprises the following steps:

specifying a number, which is at least two, of diffusion gradient pulse sequences for recording diffusion data sets using the magnetic resonance imaging apparatus such that the diffusion gradient pulse sequences have a b-matrix that describes a planar diffusion encoding that comprises precisely two intrinsic values that differ from zero, recording the diffusion data sets with the specified diffusion gradient sequences, and acquiring a trace-weighted image data set by geometric averaging of the at least two diffusion data sets, wherein the diffusion gradient pulse sequences are determined such that the sum of all the b-matrices results in the unit matrix multiplied by a factor that characterizes the diffusion weighting, in particular by a predetermined b-value and the number divided by three.

Here, the b-value is usually used as the factor that characterizes the diffusion weighting. The disclosure therefore provides the opportunity for the direct calculation of trace-weighted image data sets from at least two diffusion-weighted images, in diffusion data sets with an identical b-value, using planar diffusion encoding. This means that the b-matrices can, as this identical b-value, be multiplied by a matrix filled with e.g. rational numbers and zero. Accordingly, the method according to the disclosure provides for at least two diffusion data sets to be recorded with planar diffusion encoding and identical diffusion weighting (b-value), to calculate a trace-weighted image data set therefrom. In this way, the advantages of linear and spherical diffusion encoding are combined such that a good compromise between efficiency and contrast is achieved. Accordingly, trace-weighted image data sets can advantageously be acquired independently for each individual b-value of interest. The influence of mesoscopic orientation dispersion on the trace-weighting is reduced in comparison with linear diffusion encoding, while a higher efficiency of the diffusion encoding is immediately provided compared with spherical diffusion encoding. Just a few measurement procedures, that is, at least two, are sufficient.

Planar diffusion encoding is characterized by the fact that the b-matrix has precisely two intrinsic values that differ from zero. A trace-weighted image can be generated as a geometrical mean from a number N of diffusion data sets recorded using planar encoding $$S_{Trace}(r)=\emptyset_{n=1\ldots N}S_n(r)^{1/N} \quad (7)$$

if the b-matrices $b_n$ in turn fulfil the condition in equation (1), such that the result is $$\begin{aligned} S_{Trace}(r) &= \prod_{n=1\ldots N} S_n(r)^{1/N} \\ &= S_0(r)\exp\left(-1/N Tr\left(D(r)\sum_{n=1\ldots N} b_n\right)\right) \\ &= S_0(r)\exp(-b/3Tr(D(r))) \end{aligned} \quad (8)$$

All the b-matrices are usually symmetrical and realistic, and can therefore be shown in diagonal form. Here, compared with linear diffusion encoding:

$$b = b\begin{pmatrix} 1 & 0 & 0 \\ 0 & 0 & 0 \\ 0 & 0 & 0 \end{pmatrix}, b = b\begin{pmatrix} 0 & 0 & 0 \\ 0 & 1 & 0 \\ 0 & 0 & 0 \end{pmatrix} \text{ or } b = b\begin{pmatrix} 0 & 0 & 0 \\ 0 & 0 & 0 \\ 0 & 0 & 1 \end{pmatrix}, \quad (9),$$

the result for spherical diffusion encoding is $$b = b\begin{pmatrix} 1/3 & 0 & 0 \\ 0 & 1/3 & 0 \\ 0 & 0 & 1/3 \end{pmatrix} \quad (10)$$

and for planar diffusion encoding it is $$b = b\begin{pmatrix} \frac{x}{x+y} & 0 & 0 \\ 0 & \frac{y}{x+y} & 0 \\ 0 & 0 & 0 \end{pmatrix}, \quad (11)$$

$$b = b\begin{pmatrix} 0 & 0 & 0 \\ 0 & \frac{x}{x+y} & 0 \\ 0 & 0 & \frac{y}{x+y} \end{pmatrix} \text{ oder } b = b\begin{pmatrix} \frac{x}{x+y} & 0 & 0 \\ 0 & 0 & 0 \\ 0 & 0 & \frac{y}{x+y} \end{pmatrix},$$

where for planar diffusion encoding, the values x>0 and y>0 apply. The special case of x=y is referred to as circular diffusion encoding.

Since it is ultimately desirable to keep to a low number of measurements, that is, of recording processes for diffusion data sets, the number can usefully be two or three, with two advantageously requiring a lesser number of measurements.

The diffusion data sets can be recorded using a spin echo sequence and/or an EPI read-out technique. EPI (echo planar imaging) offers very efficient spatial encoding, which is beneficial for surveying large examination regions or those with high resolution. Spin echo techniques are already often used nowadays in diffusion imaging.

Nevertheless, it is pointed out that the method according to the disclosure can be carried out not only using spin echo sequences, but also for example using gradient echo sequences, meaning without a refocusing pulse, or also using doubly refocused spin echo sequences (meaning two refocusing pulses that are emitted, for example, after the first and before the last diffusion gradient pulse). Furthermore, magnetic resonance sequences using a stimulated echo are also possible. Apart from the EPI technique, e.g. from the single shot EPI technique, segmented EPI, turbo spin echo (TSE), multi-gradient echo and suchlike can be used as a read-out technique.

Hereafter two examples for a number N=2 and for a number N=3 are provided. If a trace-weighted image data set is to be acquired from N=2 measurements with planar diffusion encoding, the b-matrix $$b_1 = b \begin{pmatrix} 2/3 & 0 & 0 \\ 0 & 1/3 & 0 \\ 0 & 0 & 0 \end{pmatrix} \quad (12)$$

can be used for the first measurement and for the second measurement the b-matrix $$b_2 = b \begin{pmatrix} 0 & 0 & 0 \\ 0 & 1/3 & 0 \\ 0 & 0 & 2/3 \end{pmatrix} \quad (13)$$

Condition (1) is then fulfilled:

$$\sum_{n=1...2} b_n = b \begin{pmatrix} 2/3 & 0 & 0 \\ 0 & 2/3 & 0 \\ 0 & 0 & 2/3 \end{pmatrix} = N/3 b1 \quad (14)$$

The trace-weighted image data set can then be calculated from the two planar-encoded diffusion data sets $$S_{1,2}(r) = S_0(r) \exp(-\mathrm{Tr}(D(r) b_{1,2})) \quad (15)$$

according to $$S_{Trace}(r) = (S_1(r) S_2(r))^{1/2} \quad (16)$$

In the case of N=3 measurements using planar diffusion encoding, the b-matrices $$b_1 = b \begin{pmatrix} 1/2 & 0 & 0 \\ 0 & 1/2 & 0 \\ 0 & 0 & 0 \end{pmatrix} \quad (17)$$

-continued $$b_2 = b \begin{pmatrix} 0 & 0 & 0 \\ 0 & 1/2 & 0 \\ 0 & 0 & 1/2 \end{pmatrix} \quad (18)$$

$$b_3 = b \begin{pmatrix} 1/2 & 0 & 0 \\ 0 & 0 & 0 \\ 0 & 0 & 1/2 \end{pmatrix} \quad (19)$$

can be used, for example. Once again, as is clearly visible, the condition according to equation (1) has been fulfilled, $$\sum_{n=1...3} b_n = b \begin{pmatrix} 1 & 0 & 0 \\ 0 & 1 & 0 \\ 0 & 0 & 1 \end{pmatrix} = N/3 b1. \quad (20)$$

The trace-weighted image data set emerges from the now three planar-coded diffusion data sets $$S_{1,2,3}(r) = S_0(r) \exp(-\mathrm{Tr}(D(r) b_{1,2,3})) \quad (21)$$

as $$S_{Trace}(r) = (S_1(r) S_2(r) S_3(r))^{1/3}. \quad (22)$$

In the context of the present disclosure, various approaches are conceivable for the specific technical implementation of such b-matrices. While it is to acquire a diffusion gradient pulse sequence according to a double diffusion encoding scheme (DDE scheme), further conceivable variants make provision, for example, for diffusion gradient pulse sequences to be acquired by means of chronologically optimized gradient paths along two spatial directions or as a sequence of gradient pulses of the same shape and amplitude in two spatial directions. For instance, it is also conceivable here, in at least one of the diffusion gradient pulse sequences, to emit gradient pulses in a plurality of spatial directions, e.g. on a plurality of, (e.g. all) physical gradient axes simultaneously. This allows a clear improvement in the efficiency of the diffusion encoding.

The double diffusion encoding (DDE) that is preferred according to the disclosure is described, for example, in an article by Noam Shemesh at al., entitled "Conventions and nomenclature for double diffusion encoding NMR and MRI", *Magnetic Resonance in Medicine* 75 (2016), pp. 82-87. Here, for example, two pairs of diffusion gradient pulses can be applied along different encoding directions, e.g. along two different physical gradient axes (X, Y and Z). For example, it is then conceivable when embedding in a single shot spin echo magnetic resonance sequence with echoplanar read-out of one of the pairs of diffusion gradient pulses before the refocusing pulse, to subsequently emit a further pair. The time interval between the diffusion gradient pulses in a pair and the width thereof (in the case of at least substantially rectangular diffusion gradient pulses) determines the corresponding b-value, together with the gradient amplitude.

Alongside the use of a DDE sequence, it also falls within the scope of the present disclosure to use, for example, optimized chronological gradient paths along two encoding directions, as is described, for example, in the article by Filip Szczepankiewicz et al. (cited previously).

Furthermore, planar diffusion encodings can also be achieved by means of sequences of diffusion gradient pulses with an identical shape and amplitude along two spatial directions. For example, the following sequence of idealized rectangular gradient pulses and pauses of equal duration on the x- and y-axis generates a virtually circular encoding:

$$G_x = \{+1,+1,+1,-1,-1,-1,-1,-1,-1,+1,+1,+1\}$$

$$G_y = \{-1,0,-1,0,0,-1,+1,0,0,+1,0,+1\}$$

As has already been mentioned, in the technical implementation, the efficiency of planar diffusion encoding can be increased by simultaneously applying diffusion gradient pulses on a plurality of physical gradient axes. If in an example of a DDE sequence, the first gradient pair having the amplitude G is applied on the x-axis and the second gradient pair having the same amplitude is applied on the y-axis, with a time interval between them, the result is a b-matrix of $$b = b \begin{pmatrix} 1/2 & 0 & 0 \\ 0 & 1/2 & 0 \\ 0 & 0 & 0 \end{pmatrix}, \quad (23)$$

where the b-value with the gyromagnetic ratio $\gamma$, the gradient pulse width $\delta$, of the gradient pulse interval $\Delta$ for the diffusion gradient pulses in a pair, the gradient amplitude G, and ignoring gradient ramps, calculates as:

$$b = \tfrac{2}{3}\gamma^2\delta^2G^2(\Delta-\delta/3) + \tfrac{2}{3}\gamma^2\delta^2G^2(\Delta-\delta/3) = \tfrac{4}{3}\gamma^2\delta^2G^2(\Delta-\delta/3). \quad (24)$$

A more efficient encoding is obtained in this context, for example, if the first pair of diffusion gradient pulses is simultaneously applied on the x-axis (amplitude+G), y-axis (amplitude+G) and z-axis (amplitude+G/2) and the second pair of diffusion gradient pulses on the x-axis (amplitude−G), y-axis (amplitude+G/2) and z-axis (amplitude+G). The two encoding directions are orthogonal to each other and a planar, in this case even circular, diffusion encoding of the shape:

$$b_1 = b' \begin{pmatrix} 4/9 & 1/9 & -1/9 \\ 1/9 & 5/18 & 2/9 \\ -1/9 & 2/9 & 5/18 \end{pmatrix}, \quad (25)$$

is obtained after diagonalization $$b_1 = b' \begin{pmatrix} 0 & 0 & 0 \\ 0 & 1/2 & 0 \\ 0 & 0 & 1/2 \end{pmatrix}, \quad (26)$$

where $$b' = 4/3\gamma^2\delta^2 G_{\mathit{eff}}^2(\Delta-\delta/3). \quad (27)$$

Here the equation:

$$G_{\mathit{eff}}^2 = G^2(1+1+\tfrac{1}{4}) = 9/4 G^2 \quad (28)$$

applies, such that the efficiency of the diffusion encoding is higher by the factor 2.25.

Combined with a second and third measurement, the gradient pairs with (+G, −G, +G/2) and (−G/2, +G, −G) or with (−G, −G/2, +G) and (+G/2, +G, +G) are applied; this means using the b-matrices:

$$b_2 = b' \begin{pmatrix} 5/18 & -3/9 & 2/9 \\ -3/9 & 4/9 & -3/9 \\ 2/9 & -3/9 & 5/18 \end{pmatrix} \quad (29)$$

and $$b_3 = b' \begin{pmatrix} 5/18 & 2/9 & -1/9 \\ 2/9 & 5/18 & 1/9 \\ -1/9 & 1/9 & 4/9 \end{pmatrix}, \quad (30)$$

a corresponding trace-weighted image data set can then be generated by geometric averaging.

Yet, in this context, the DDE encoding directions do not necessarily have to be perpendicular to each other. If this precondition is no longer required, there is a new degree of freedom that allows further increases in efficiency. For example, the first pair of diffusion gradient pulses can be applied simultaneously with (+G, +G, +G) and the second pair simultaneously with [−G, −G, +G). The encoding directions are now no longer orthogonal, and a planar diffusion encoding of the shape $$b_1 = b' \begin{pmatrix} 1/3 & 1/3 & 0 \\ 1/3 & 1/3 & 0 \\ 0 & 0 & 1/3 \end{pmatrix}, \quad (31)$$

is obtained after diagonalization $$b_1 = b' \begin{pmatrix} 0 & 0 & 0 \\ 0 & 1/3 & 0 \\ 0 & 0 & 2/3 \end{pmatrix}, \quad (32)$$

where this again results in b' according to equation (27). However, with $$G_{\mathit{eff}}^2 = G^2(1+1+1) = 3G^2 \quad (33),$$

the efficiency of the diffusion encoding is increased again here even by a factor of 3.

In combination with a second measurement, in which the gradient pairs with (+G, −G, −G) and (−G, +G, −G) are applied, that is, with the b-matrix:

$$b_2 = b' \begin{pmatrix} 1/3 & -1/3 & 0 \\ -1/3 & 1/3 & 0 \\ 0 & 0 & 1/3 \end{pmatrix}, \quad (34)$$

a trace-weighted image data set can be generated in turn by geometric averaging.

In an advantageous further development of the present disclosure, provision is made that in the case of imaging gradient pulses emitted mainly on a first physical gradient axis for recording diffusion data sets, the distribution of the diffusion gradient pulses is selected such that, for each diffusion gradient pulse sequence, they are emitted mainly on a physical gradient axis that is different from the first physical gradient axis. In other words, for measurements in which the imaging gradients are principally applied on a specific physical gradient axis, that is, on the first physical gradient axis, the load of the planar diffusion encoding gradient pulses is advantageously distributed onto the other, in particular second and third, physical gradient axes. In this way, depending on the gradient apparatus or gradient hardware used, more power is available for the imaging portions.

For example, in the case of an EPI read-out, the main load is on the read-out gradient axis, for example on the x-axis, which can be kept as free as possible from the load of the planar diffusion encoding gradient pulses.

In a specific design variant, where the number of diffusion gradient pulse sequences in the first gradient pulse sequence is two, provision can be made for a diffusion gradient pulse pair with a predetermined amplitude to be emitted on a second physical gradient axis and for a diffusion gradient pulse pair with the predetermined amplitude divided by the square root of two to be emitted on the first gradient axis and in the case of the second gradient pulse sequence, for a diffusion gradient pulse pair with the predetermined amplitude to be emitted on a third physical gradient axis and for a diffusion gradient pulse pair with the predetermined amplitude divided by the square root of two to be emitted on the first gradient axis. If the first physical gradient axis is the x-axis for example, two such DDE measurements can be carried out such that, in a first measurement, the first diffusion gradient pulse pair with the amplitude $G/\sqrt{2}$ is emitted on the x-axis, and a second diffusion gradient pulse pair with the amplitude G is emitted on the y-axis. In the second measurement, a first diffusion gradient pulse pair with the amplitude $G/\sqrt{2}$ is emitted on the x-axis, and a second diffusion gradient pulse pair with the amplitude G is emitted on the z-axis. Although a load is then exerted on the x-axis in both measurements, it is only with a reduced amplitude.

It should also be mentioned at this point that it would also be basically conceivable for trace-weighted image data sets to be acquired from the combination of diffusion data sets with linear and planar diffusion encoding. For example, a first measurement with planar diffusion encoding $$b_1 = b \begin{pmatrix} 1/2 & 0 & 0 \\ 0 & 1/2 & 0 \\ 0 & 0 & 0 \end{pmatrix} \quad (35)$$

can be used, while a second measurement with linear diffusion encoding $$b_2 = b' \begin{pmatrix} 0 & 0 & 0 \\ 0 & 0 & 0 \\ 0 & 0 & 1 \end{pmatrix} \quad (36)$$

is carried out, where b'=b/2. In order to implement this second measurement, $G'=G/\sqrt{2}$ can be selected in a DDE diffusion gradient pulse sequence, but it is also possible to select SDE (single diffusion encoding) for the second measurement. In each case, the condition set out in equation (1) is then fulfilled.

Similarly, combinations of planar with ellipsoid diffusion encodings of the shape $$b = b \begin{pmatrix} \frac{x}{x+y+z} & 0 & 0 \\ 0 & \frac{y}{x+y+z} & 0 \\ 0 & 0 & \frac{z}{x+y+z} \end{pmatrix} \quad (37)$$

are also basically conceivable, in which case x, y and z are not identical.

In addition to the method, the present disclosure also relates to a magnetic resonance imaging apparatus, comprising a control facility that is implemented to execute the method according to the disclosure. All the statements regarding the method embodiments according to the disclosure can be applied by analogy to the magnetic resonance imaging apparatus embodiments according to the disclosure, such that with this facility the advantages that have already been mentioned can also be retained for the magnetic resonance imaging apparatus.

Here, the control facility can comprise at least one processor (e.g. professing circuitry) and/or a memory or other suitable storage device. In practice, provision can be made, for example, for the control facility to include a specification unit (e.g. specification processing circuitry) for specifying the diffusion gradient pulse sequences, a sequencing unit (e.g. sequencing processing circuitry) for recording the diffusion data sets, and a determination unit (determination processing circuitry) for calculating the trace-weighted image data set from the diffusion data sets.

A computer program according to the disclosure is, for example, loadable into a memory (e.g. a non-transitory computer-readable medium) of a control facility of a magnetic resonance imaging apparatus and comprises a program and/or executable instructions, which carry out the steps of one or more of the method embodiments according to the disclosure when the computer program is executed in the control facility of the magnetic resonance imaging apparatus. The computer program can be stored on an electronically readable data carrier according to the disclosure, which therefore includes electronically readable control information, and which includes at least one computer program according to the disclosure and which is implemented such that, when the electronically readable data carrier is used in a control facility of a magnetic resonance imaging apparatus, this control facility can carry out the steps of the one or more of the method embodiments according to the disclosure. The electronically readable data carrier may be e.g. a non-transitory data carrier, for example a CD-ROM.

BRIEF DESCRIPTION OF THE DRAWINGS/FIGURES

Further advantages and details of the disclosure will emerge from the embodiments that are described hereinafter and from the drawings.

Figure 2:
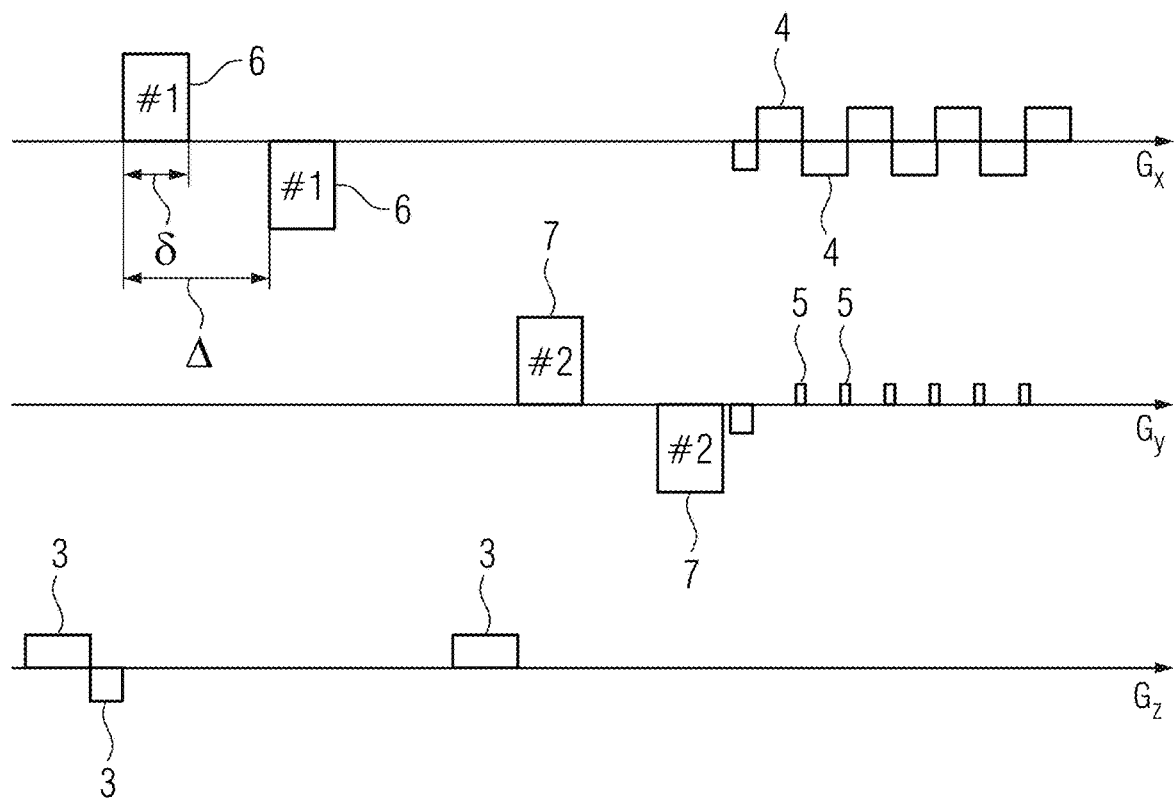
Figure 3:
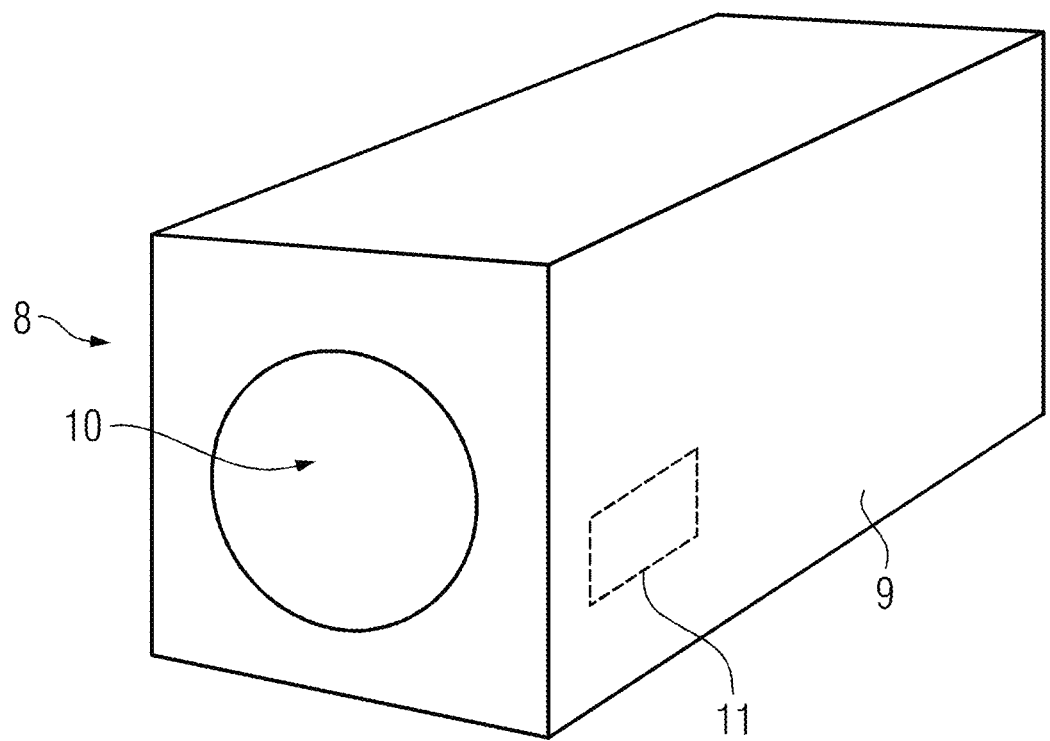
Figure 4:
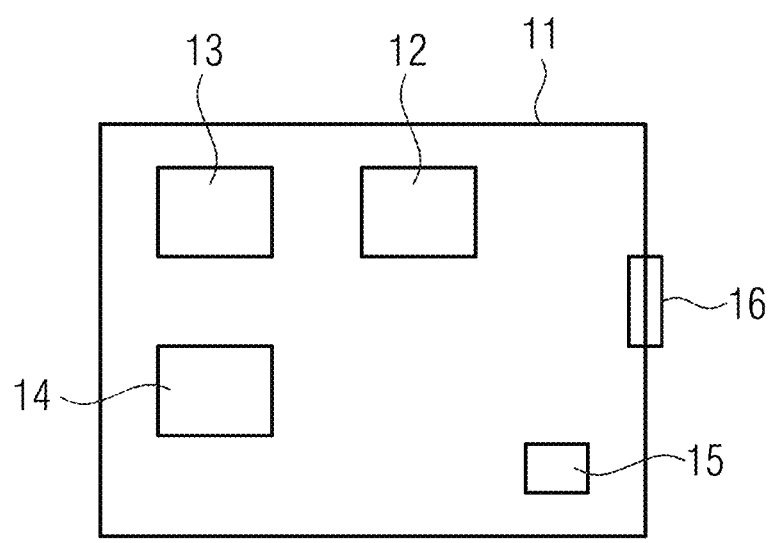

FIG. 1 illustrates an example flow according to one or more embodiments of the disclosure, FIG. 2 illustrates an example sequencing diagram for recording a diffusion data set according to one or more embodiments of the disclosure, FIG. 3 illustrates an example magnetic resonance imaging apparatus according to one or more embodiments of the disclosure, and FIG. 4 illustrates an example functional design of a controller for the magnetic resonance imaging apparatus according to one or more embodiments of the disclosure.

DETAILED DESCRIPTION

FIG. 1 shows a general outline of a flow for an exemplary embodiment of the method according to the disclosure. This may be used for diffusion imaging, e.g. for acquiring a trace-weighted image data set relating to an examination region of a patient.

In step S1, the diffusion gradient pulse sequences to be used are established hereafter such that a planar diffusion encoding is provided in all the diffusion gradient pulse sequences to be used, e.g. two or three diffusion gradient pulse sequences, meaning that the diffusion gradient pulse sequences are specified such that the relevant b-matrix thereof includes precisely two intrinsic values that differ from zero. Here, the b-matrices fulfill the condition described in equation (1), according to which the sum of all the b-matrices results in the unit matrix multiplied by a predetermined b-value and by the number divided by three.

Various options exist for the specific technical implementation of the diffusion gradient sequences, for example, the determination of chronologically optimized gradient paths along two spatial directions, the determination of a sequence of gradient pulses in the same shape and amplitude in two spatial directions, etc. As an example, an embodiment includes the diffusion gradient pulse sequences being determined as DDE (double diffusion encoding) sequences. Moreover, it can even be taken into account at this stage which magnetic resonance sequence is to be used for the imaging portion, with a spin echo sequence with single-shot EPI read-out being used as an example in the present case.

FIG. 2 shows an exemplary sequencing diagram, in which a DDE diffusion gradient pulse sequence is incorporated into a single-shot spin echo sequence with echoplanar read-out. Here RF/ADC denotes the radio frequency activity, $G_x$ shows gradient pulses on a first physical gradient axis, in this case the x-axis, with $G_y$ and $G_z$ used accordingly for the y-axis as the second physical gradient axis and the z-axis as the third physical gradient axis. It can be seen that the single-shot spin echo sequence includes a radio frequency excitation pulse 1 as well as a radio frequency refocusing pulse 2. Imaging gradient pulses 3 are assigned thereto, as is basically known, in this case as slice selection gradients along the z-axis. In the read-out module the main gradient load in the case of the imaging gradient pulse 4 is on the x-axis as a read-out direction, while as is known, further imaging gradient pulses 5 are required on the y-axis in particular for exchanging the k-space cells.

Planar diffusion encoding mainly uses two pairs of diffusion gradient pulses 6, 7, wherein the first pair of diffusion gradient pulses 6 is emitted along the x-axis, and the second pair of diffusion gradient pulses 7 along the y-axis. The diffusion gradient pulse sequence with the diffusion gradient pulses 6, 7 that is shown in FIG. 2 produces a b-matrix of the shape described by equation (23), resulting in the b-value according to equation (24), as already explained above. The diffusion gradient pulse width δ and the interval between the diffusion gradient pulses 6, 7 in a pair, Δ, are likewise shown in FIG. 2.

The measurement shown in FIG. 2 is suitable, for example, as a first measurement when recording three diffusion data sets, it being possible there to use the same amplitudes G of the diffusion gradient pulses 6, 7.

In a different example, if the number N is only two, for instance when producing a b-matrix with the shape $$b = b \begin{pmatrix} 2/3 & 0 & 0 \\ 0 & 1/3 & 0 \\ 0 & 0 & 0 \end{pmatrix}, \quad (38)$$

it is possible to continue to use the amplitude G for the diffusion gradient pulses 6, for example, and for the other pair of diffusion gradient pulses 7, however, to use the amplitude $G/\sqrt{2}$. In this case the b-value of the entire diffusion gradient pulse sequence is $$b = \tfrac{2}{3}\gamma^2\delta^2 G^2(\Delta-\delta/3) + \tfrac{1}{3}\gamma^2\delta^2 G^2(\Delta-\delta/3) = \gamma^2\delta^2 G^2(\Delta-\delta/3). \quad (39)$$

FIG. 2 shows, for greater simplicity, an approach using diffusion gradient pulse pairs along physical gradient axes, in the example shown in FIG. 2 along the x-axis and the y-axis. However, the measures to increase the diffusion efficiency that are described with respect to equations (26) to (34) can be used and/or since in the sequencing diagram in FIG. 2 a main load is exerted on the x-axis due to the EPI read-out, the gradient load on this x-axis can be reduced in a targeted manner, as described.

As soon as the diffusion gradient pulse sequences have been established accordingly, the diffusion data sets can be recorded in step S2, see again FIG. 1, using one of the diffusion gradient pulse sequences. In step S3, the trace-weighted image data set $S_{Trace}$ can then be acquired according to equation (7) as a geometric average of the diffusion data sets.

FIG. 3 shows a sketch of the principle involved in a magnetic resonance imaging apparatus 8 according to embodiments of the disclosure. The magnetic resonance imaging apparatus may alternatively be referred to as a magnetic resonance imager or simply an imager and may comprise, as is basically known, a main magnet unit 9 (or main magnet or simply magnet), in which a patient support 10 is implemented, into which a patient can be moved for examination using a patient couch that is not shown here in further detail. Surrounding the patient couch, a gradient coil array, not shown in greater detail here for reasons of clarity, is usually provided, with gradient coils for the x-axis, the y-axis, and the z-axis. Both imaging gradient pulses 3, 4, 5 and diffusion gradient pulses 6, 7 can be emitted using this gradient coil array.

The operation of the magnetic resonance imaging apparatus 8 may be controlled by means of a control facility 11, which is indicated, and which may also be implemented to execute the method embodiments according to the disclosure. The control facility may alternatively be referred to herein as a controller, control circuitry, or control computer 11. FIG. 4 shows the functional structure of the control facility 11 in further detail. The control facility 11 initially comprises, as is basically known, a sequencing unit, sequencer, or sequencing circuitry 12, via which the other components of the magnetic resonance imaging apparatus 8 are activated to record magnetic resonance data according to a magnetic resonance sequence. The diffusion data sets can therefore also be recorded in step S2 by means of the sequencing unit 12. To this end, the b-matrices to be used and the diffusion gradient pulse sequences that technically implement these in practice are to be specified beforehand by means of a specification unit, specifier, or specification circuitry 13. It should be pointed out here that a single specification process, that is, e.g. a single execution of step S1 according to FIG. 1, is conceivable before a plurality of measurements, meaning that diffusion gradient pulse sequences specified on one occasion can be used on a plurality of occasions. The control facility 11 further comprises a determination unit, determiner, or determination circuitry 14 for acquiring the trace-weighted image data set according to step S3.

Moreover, said unit can also comprise memory 15, in which for example, the specified diffusion gradient pulse sequences and the diffusion data sets can be stored at least temporarily, and also, of course, the final result. This result, that is, the trace-weighted image data set, can also be issued via an interface 16 in the control facility 11, wherein the control facility 11 can of course also comprise a display unit to issue the trace-weighted image data set, for example on a display device of the magnetic resonance imaging apparatus 8. The memory 15 may comprise a non-transitory computer-readable medium having executable instructions stored thereon, as discussed herein, which may be executed by one or more processors and/or components of the control facility 11 to functionally realize any of the embodiments as discussed herein. The functional units, that is, the sequencing unit 12, the specification unit 13, and the acquisition unit 14, may be implemented by at least one processor in the control facility 11, e.g. one or more circuits, processing circuitry, etc., which may work independently as hardware components and/or in conjunction with one or more executable instructions (e.g. via execution of instructions stored in the memory 15), or combinations thereof.

Finally, it should also be pointed out here that in the context of the present disclosure it is also possible to acquire a plurality of trace-weighted image data sets for different b-values, e.g. in order to derive therefrom further data and parameters, for example relating to the diffusion tensor and/or to the apparent diffusion coefficient (ADC).

Although the disclosure has been illustrated and described in greater detail with the preferred embodiments, the disclosure is not restricted to the examples disclosed, and other variants can be derived therefrom by a person skilled in the art, without going beyond the scope of the disclosure.

What is claimed is:

1. A method for performing diffusion imaging with a magnetic resonance imaging apparatus, comprising:
    determining a number of diffusion gradient pulse sequences for recording respective planar-encoded diffusion data sets using the magnetic resonance imaging apparatus such that each one of the diffusion gradient pulse sequences has a respective b-matrix that is defined in accordance with a planar diffusion encoding having two intrinsic values that differ from zero, the number of the diffusion gradient pulse sequences being at least two,
    wherein the diffusion gradient pulse sequences each comprises diffusion encoding gradient pulses;
    recording the planar-encoded diffusion data sets in accordance with each respective one of the number of diffusion gradient pulse sequences; and
    acquiring a trace-weighted image data set by performing geometric averaging of the recorded planar-encoded diffusion data sets,
    wherein the number of diffusion gradient pulse sequences is determined such that a sum of the b-matrices for each respective one of the number of diffusion gradient pulse sequences results in a unit matrix being multiplied by (i) a predetermined b-value factor that characterizes the diffusion weighting, and (ii) the number of diffusion gradient pulse sequences divided by three.

2. The method as claimed in claim 1, wherein the number of diffusion gradient pulse sequences is three.

3. The method as claimed in claim 1, wherein the number of diffusion gradient pulse sequences are encoded in accordance with a circular encoding.

4. The method as claimed in claim 1, wherein the planar-encoded diffusion data sets are recorded using a spin echo sequence read-out technique.

5. The method as claimed in claim 1, wherein the planar-encoded diffusion data sets are recorded using an echo-planar imaging (EPI) read-out technique.

6. The method as claimed in claim 1, further comprising:
    acquiring the number of diffusion gradient pulse sequences in two spatial directions according to a double diffusion encoding scheme.

7. The method as claimed in claim 1, further comprising:
    acquiring the number of diffusion gradient pulse sequences according to chronologically optimized gradient paths along two spatial directions.

8. The method as claimed in claim 1, further comprising:
    acquiring the number of diffusion gradient pulse sequences as a sequence of gradient pulses having the same shape and amplitude.

9. The method as claimed in claim 1, further comprising:
    simultaneously emitting at least one of the number of diffusion gradient pulse sequences in each one of plurality of physical gradient axes.

10. The method as claimed in claim 1, wherein at least one of the number of diffusion gradient pulse sequences includes imaging gradient pulses emitted on a first physical gradient axis for recording the planar-encoded diffusion data sets, and further comprising:
    for the at least one of the number of diffusion gradient pulse sequences including the imaging gradient pulses emitted on the first physical gradient axis, determining a distribution of diffusion gradient pulses such that the diffusion gradient pulses are emitted on a physical gradient axis that differs from the first physical gradient axis.

11. The method as claimed in claim 10, further comprising:
    emitting in a first gradient pulse sequence of the number of the diffusion gradient pulse sequences (i) a diffusion gradient pulse pair with a predetermined amplitude on a second physical gradient axis, and (ii) a diffusion gradient pulse pair with the predetermined amplitude divided by the square root of two on the first physical gradient axis; and
    emitting in a second gradient pulse sequence of the number of the diffusion gradient pulse sequences (i) a diffusion gradient pulse pair with the predetermined amplitude on a third physical gradient axis, and (ii) a diffusion gradient pulse pair with the predetermined amplitude divided by the square root of two on the first physical gradient axis.

12. A magnetic resonance imaging apparatus for performing diffusion imaging of an examination region of a patient, comprising:
    a main magnet;
    a patient support configured to receive the patient; and
    control circuitry configured to:
        determine a number of diffusion gradient pulse sequences for recording respective planar-encoded diffusion data sets using the magnetic resonance imaging apparatus such that each one of the diffusion gradient pulse sequences has a respective b-matrix that is defined in accordance with a planar diffusion encoding having two intrinsic values that differ from zero, the determined number of the diffusion gradient pulse sequences being at least two,
        wherein the diffusion gradient pulse sequences each comprises diffusion encoding gradient pulses;
        record the planar-encoded diffusion data sets in accordance with each respective one of the number of diffusion gradient pulse sequences; and
        acquire a trace-weighted image data set by performing geometric averaging of the recorded planar-encoded diffusion data sets, wherein the control circuitry is further configured to determine the number of diffusion gradient pulse sequences such that a sum of the b-matrices for each respective one of the number of diffusion gradient pulse sequences results in a unit matrix being multiplied by (i) a predetermined b-value factor that characterizes the diffusion weighting, and (ii) the number of diffusion gradient pulse sequences divided by three.

13. A non-transitory computer readable medium having instructions stored thereon that, when executed by a controller of a magnetic resonance imaging apparatus, cause the magnetic resonance imaging apparatus to:

determine a number of diffusion gradient pulse sequences for recording respective planar-encoded diffusion data sets using the magnetic resonance imaging apparatus such that each one of the diffusion gradient pulse sequences has a respective b-matrix that is defined in accordance with a planar diffusion encoding having two intrinsic values that differ from zero, the determined number of the diffusion gradient pulse sequences being at least two, wherein the diffusion gradient pulse sequences each comprises diffusion encoding gradient pulses;

record the planar-encoded diffusion data sets in accordance with each respective one of the number of diffusion gradient pulse sequences; and acquire a trace-weighted image data set by performing geometric averaging of the recorded planar-encoded diffusion data sets, wherein the number of diffusion gradient pulse sequences is determined such that a sum of the b-matrices for each respective one of the number of diffusion gradient pulse sequences results in a unit matrix being multiplied by (i) a predetermined b-value factor that characterizes the diffusion weighting, and (ii) the number of diffusion gradient pulse sequences divided by three.

14. The method as claimed in claim 1, wherein acquiring the trace-weighted image data set comprises independently acquiring, for each predetermined b-value factor that characterizes a respective diffusion gradient pulse sequence of the diffusion gradient pulse sequences, trace-weighted image data.

15. The method as claimed in claim 1, wherein an influence of mesoscopic orientation dispersion on the trace-weighting data set is less than a trace-weighting data set acquired via linear diffusion encoding.

* * * * *